United States Patent [19]

Krueger et al.

[11] 4,009,204
[45] Feb. 22, 1977

[54] PROCESS OF PRODUCING CRYSTALLINE NITRILO TRIS-(METHYLENE PHOSPHONIC ACID)

[75] Inventors: Friedrich Krueger, Edingen; Lieselotte Bauer, Bad Duerkheim, both of Germany

[73] Assignee: Joh. A. Benckiser GmbH, Ludwigshafen am Rhein, Germany

[22] Filed: Mar. 18, 1971

[21] Appl. No.: 125,852

[30] Foreign Application Priority Data

Mar. 20, 1970 Germany .......................... 2013372

[52] U.S. Cl. ............................................ 260/502.5
[51] Int. Cl.² ........................................ C07F 9/38
[58] Field of Search ................................ 260/502.5

[56] References Cited

UNITED STATES PATENTS

| | | | |
|---|---|---|---|
| 2,338,987 | 1/1944 | Wetzol | 260/502.5 |
| 3,288,846 | 11/1966 | Isani et al. | 260/502.5 |
| 3,476,799 | 11/1969 | Vogt et al. | 260/502.5 |
| 3,549,728 | 12/1970 | Balde et al. | 260/502.5 |

FOREIGN PATENTS OR APPLICATIONS

| | | | |
|---|---|---|---|
| 1,142,294 | 2/1969 | United Kingdom | 260/502.5 |
| 1,023,785 | 3/1966 | United Kingdom | 260/502.5 |

OTHER PUBLICATIONS

Cline, "Manufacture of Urea," (1951), pp. 35–42.

*Primary Examiner*—Joseph E. Evans
*Attorney, Agent, or Firm*—Erich M. H. Radde

[57] ABSTRACT

Pure, crystalline nitrilo tris-(methylene phosphonic acid) is produced in a high yield by reacting lower aliphatic acid amides with formaldehyde and phosphorus trihalogenide, preferably phosphorus trichloride.

8 Claims, No Drawings

PROCESS OF PRODUCING CRYSTALLINE NITRILO TRIS-(METHYLENE PHOSPHONIC ACID)

BACKGROUND OF THE INVENTION

1. Field of the Invention

The present invention relates to an improved process of nitrilo tris-(methylene phosphonic acid) and more particularly to a process of producing substantially pure, crystalline nitrilo tris-(methylene phosphonic acid).

2. Description of the Prior Art

A number of processes of producing nitrilo tris-(methylene phosphonic acid) are known. Thus said compound is obtained according to German published application No. 1,214,229 by reacting ammonium chloride, formaldehyde, and phosphorous acid in the proportion 1:3:3. The yield of pure, solid compound is not given. It has merely been determined by means of the nuclear magnetic resonance spectrum (NMR-spectrum) of the reaction solution that 85% of the orthophosphorous acid have been reacted to form the desired N-C-P linkage.

Subsequently it has been reported in German published application No. 1,259,337 that, on determining the yield by NMR-analysis of the reaction solution, byproducts are included and that pure nitrilo tris-(methylene phosphonic acid) precipitates from the reaction solution obtained according to German published application No. 1,214,229 in crystalline form only very slowly and within several days. The yield does not exceed about 46%. It is furthermore stated in said published application No. 1,259,337 that the yield can be increased to 86% by reacting an excess of phosphorous acid between 20 and 80% and preferably between 30 and 50%. However, even when proceeding in this manner, crystalline nitrilo tris-(methylene phosphonic acid) precipitates only very slowly, namely at 20° C. within 16 hours.

British Pat. No. 1,142,294 discloses the preparation of nitrilo tris-(methylene phosphonic acid) by reacting ammonium chloride, 37% aqueous formaldehyde solution, and phosphorus trichloride. The yield as given in said British Pat. No. 1,142,294 was also determined by analyzing the reaction solution. Isolation of the crystalline compound has not been described in the examples.

SUMMARY OF THE INVENTION

It is one object of the present invention to provide a simple and improved process of producing pure, crystalline nitrilo tris-(methylene phosphonic acid) in a high yield and in a short time without causing the reaction solution to stand for a prolonged period of time and/or without having to concentrate the reaction solution.

Other objects of the present invention and advantageous features thereof will become apparent as the description proceeds.

In principle the new process of producing nitrilo tris-(methylene phosphonic acid) according to the present invention comprises reacting lower aliphatic mono- or dicarboxylic acid amides, preferably formamide, oxamide, and urea, with formaldehyde, preferably in aqueous solution, and with a phosphorus trihalogenide, preferably with phosphorus trichloride.

The process according to the present invention has the advantage over the known processes that nitrilo tris-(methylene phosphonic acid) crystallized already during the reaction and/or during cooling the reaction solution in a high yield so that prolonged standing and/or concentrating of the reaction solution are not required. In addition thereto the yield of the solid, pure compound is considerably increased over that obtained according to the known processes.

According to a preferred embodiment of the present invention the reaction is carried out by first placing the acid amide and formaldehyde into the reaction vessel, slowly adding drop by drop phosphorus trichloride thereto while cooling, and heating the reaction mixture on the boiling water bath for one hour to two hours. After cooling the reaction solution, the crystallized nitrilo tris-(methylene phosphonic acid) is filtered off by suction. The yield is about 80%.

It is, of course, also possible to carry out the reaction in another order of addition of the reactants. Thus the acid amide can be added slowly to the mixture of formaldehyde and phosphorus trichloride.

When using ammonium chloride in this reaction, in place of the acid amide, as this has been described heretofore, nitrilo tris-(methylene phosphonic acid) crystallizes only after allowing the reaction solution to stand for a prolonged period of time. Its yield is much lower and does not exceed 65%.

The following Table illustrates the noteworthy advantage achieved by proceeding according to the process of this invention in comparison to the known processes.

Table

Comparison of the yield of nitrilo tris-(methylene phosphonic acid) and the time required for crystallizing said compound when produced according to the present invention with an acid amide and according to the known processs with ammonium chloride.

| Nitrogen Reactant | Formaldehyde 30% solution | Phosphorus trichloride | Water added | Yield % | Crystallization |
|---|---|---|---|---|---|
| Formamide | 3.15 moles | 3 moles | 20 ml. | 73.2 | during reaction |
|  |  |  |  | 69.5 | on cooling |
|  |  |  |  | 74.4 | on cooling |
| Ammonium chloride | 3.15 moles | 3 moles | 20 ml. | 58.8 | after 15 hours |
|  |  |  |  | 60.0 | " |
|  |  |  |  | 58.2 | " |
| Formamide | 3.0 moles | 3 moles | — | 72.2 | on cooling |
|  |  |  |  | 80.0 | " |
|  |  |  |  | 78.6 | " |
| Oxamide | 6.0 moles | 6 moles | — | 70.5 | on cooling |
|  |  |  |  | 69.8 | " |
|  |  |  |  | 71.0 | during reaction |
| Ammonium chloride | 3.0 moles | 3 moles | — | 65.0 | after 15 hours |
|  |  |  |  | 64.3 | " |
|  |  |  |  | 64.9 | " |
| Formamide | 3.0 moles | 3 moles + 30% excess | — | 80.4 | during reaction |
|  |  |  |  | 64.2 | on cooling |
| Ammonium chloride | 3.0 moles | 3 moles + 30% excess | — | 59.4 | after 15 hours |
|  |  |  |  | 52.3 | " |

The crystallized compounds were filtered off by suction washed with acetone, and dried.

This Table clearly shows not only that a substantially higher yield is achieved when proceeding according to the present invention but also that the time of crystallization is very considerably reduced in comparison with the known processes.

DESCRIPTION OF THE PREFERRED EMBODIMENTS

The following examples serve to illustrate the present invention without, however, limiting the same thereto.

EXAMPLE 1

412.5 g. of phosphorus trichloride (3 moles) are slowly added drop by drop to a solution of 45 g. of formamide (1 mole) in 300 g. of 30% formaldehyde solution (3 moles) and 20 ml. of water. The reaction mixture is then slowly heated and heating in the boiling water bath is continued for one to two hours. On cooling the reaction solution, nitrilo tris-(methylene phosphonic acid) crystallizes. It is filtered off by suction, washed with acetone, and dried.

Yield: 219 g. corresponding to 73.2% of the theoretical yield.

When using, in place of 1 mole of formamide, 53.5 g. of ammonium chloride (1 mole), nitrilo tris-(methylene phosphonic acid) crystallizes only after allowing the reaction mixture to stand for 15 hours. 175 g. of nitrilo tris-(methylene phosphonic acid) corresponding to 58.8% of the theoretical yield are obtained after filtering off the crystallized compound and washing with acetone.

Nuclear magnetic resonance spectra and thin layer chromatograms were prepared of both products. They proved to be identical.

EXAMPLE 2

412 g. of phosphorus trichloride (3 moles) are slowly added drop by drop to a solution of 44 g. of oxamide (0.5 mole) in 300 g. of 30% formaldehyde solution (3 moles) while stirring and cooling with water. The reaction mixture is then carefully heated in a water bath and heating in the boiling water bath is continued for 1½ hours. Nitrilo tris-(methylene phosphonic acid) starts to precipitate during heating. After cooling the reaction solution, the crystalline precipitate is filtered off by suction, washed with acetone, and dried.

Yield: 210.8 g. corresponding to 70.5% of the theoretical yield.

EXAMPLE 3

When using, in place of oxamide, 30 g. of urea (0.5 mole) and otherwise proceeding as described in Example 2, crystalline nitrilo tris-(methylene phosphonic acid) is obtained in about the same yield.

Preferably the concentration of the formaldehyde solution is between 25 and 40%, by weight. In place of aqueous formaldehyde solution, there may also be employed its trimer, trioxane or its polymers such as paraformaldehyde although formaldehyde solution have proved to be preferred.

In place of phosphorus trichloride as used in the examples, there can also be employed equimolecular amounts of phosphorus tribromide or phosphorus triiodide.

It is also possible to carry out the reaction at a higher temperature than that of the boiling water bath, for instance, at a temperature between 110° and 140° C. although such a procedure will require operating in a closed vessel.

As shown in the Table the formaldehyde as well as the phosphorus trihalogenide can be used in excess over the required amount.

Nitrilo tris-(methylene phosphonic acid) is an excellent complexing agent for polyvalent metal ions, such as calcium, magnesium, iron, and the like ions. When used in amounts smaller than required stoichiometrically, nitrilo tris-(methylene phosphonic acid) is a useful agent for stabilizing the hardness of water at room temperature and also at higher temperatures. Nitrilo tris-(methylene phosphonic acid) is stable and does not hydrolyze. Therefore, it can be incorporated into solid and fluid products to be employed in aqueous media regardless whether they are used under acid, alkaline, or neutral reaction conditions.

We claim:

1. In a process of producing substantially pure, crystalline nitrilo tris-(methylene phosphonic acid), the steps which comprise
   a. slowly adding a phosphorus trihalogenide selected from the group consisting of phosphorus trichloride, phosphorus tribromide, and phosphorus triiodide to an aqueous solution of formaldehyde and a lower aliphatic acid amide selected from the group consisting of formamide and oxamide at room temperature, while stirring, the proportion of formaldehyde to phosphorus trihalogenide to acid amide calculated for one acid amide group being about 3:3:1,
   b. slowly increasing the temperature of the resulting reaction mixture to at least the temperature of the boiling water bath,
   c. heating the reaction mixture at a temperature between about 100° and about 140° C. to complete reaction,
   d. cooling the reaction solution to room temperature, and
   e. separating the resulting crystallized nitrilo tris-(methylene phosphonic acid) precipitated from the reaction solution on cooling.

2. The process of claim 1 in which the acid amide is formamide.

3. The process of claim 1, in which the acid amide is oxamide.

4. The process of claim 1, in which formaldehyde is reacted in the form of its aqueous solution.

5. The process of claim 1, in which the aqueous formaldehyde solution has a formaldehyde content not substantially exceeding 40% by weight.

6. The process of claim 1, in which the molecular proportion of formaldehyde to phosphorus trihalogenide to the acid amide calculated for one acid amide group is about 3:3:1.

7. The process of claim 1, in which the phosphorus trihalogenide is phosphorus trichloride.

8. The process of claim 1, in which the phosphorus trihalogenide is phosphorus trichloride, the aqueous formaldehyde solution is a solution of a formaldehyde content between about 25 and about 40%, by weight, and the reaction temperature in step (c) is the temperature of the boiling water bath.

* * * * *